(12) United States Patent
Becher et al.

(10) Patent No.: US 8,801,778 B2
(45) Date of Patent: Aug. 12, 2014

(54) IMPLANT WITH A BASE BODY OF A BIOCORRODIBLE ALLOY

(71) Applicant: Biotronik VI Patent AG, Baar (CH)

(72) Inventors: Baerbel Becher, Rostock (DE); Carsten Momma, Rostock (DE); Daniel Lootz, Rostock (DE); Antje Quade, Rowa (DE); Andreas Ohl, Hohendorf (DE); Karsten Schroeder, Greifswald (DE)

(73) Assignee: BIOTRONIK VI Patent AG, Baar (CH)

( * ) Notice: Subject to any disclaimer, the term of this patent is extended or adjusted under 35 U.S.C. 154(b) by 0 days.

(21) Appl. No.: 13/758,639

(22) Filed: Feb. 4, 2013

(65) Prior Publication Data

US 2013/0218265 A1 Aug. 22, 2013

Related U.S. Application Data

(63) Continuation-in-part of application No. 12/339,965, filed on Dec. 19, 2008, now abandoned.

(30) Foreign Application Priority Data

Dec. 20, 2007 (DE) .......................... 10 2007 061 647

(51) Int. Cl.
*A61F 2/06* (2013.01)
(52) U.S. Cl.
USPC ......................................... 623/1.46; 623/1.38
(58) Field of Classification Search
USPC ............................. 623/1.1, 1.38, 1.46, 23.75; 427/2.24–2.29
See application file for complete search history.

(56) References Cited

U.S. PATENT DOCUMENTS

| | | | |
|---|---|---|---|
| 5,246,451 | A | 9/1993 | Trescony et al. |
| 6,156,435 | A | 12/2000 | Gleason et al. |
| 2004/0063805 | A1 | 4/2004 | Pacetti et al. |
| 2007/0009565 | A1 | 1/2007 | Pacetti et al. |
| 2007/0172666 | A1 | 7/2007 | Denes et al. |

FOREIGN PATENT DOCUMENTS

| | | |
|---|---|---|
| DE | 19604173 C2 | 8/1997 |
| DE | 19731021 A1 | 1/1999 |
| DE | 10253634 A1 | 5/2004 |
| DE | 102006038231 A1 | 2/2008 |
| EP | 0560849 B1 | 9/1993 |
| EP | 0842207 B1 | 7/1998 |
| EP | 0993308 B1 | 4/2000 |
| WO | 8911836 A1 | 12/1989 |
| WO | 2005051453 A1 | 6/2005 |

OTHER PUBLICATIONS

Verweire et al., Evaluation of fluorinated polymers as coronary stent coating, Journal of Materials Science: Materials in Medicine 11 (2000) 207-212.

*Primary Examiner* — Howie Matthews
(74) *Attorney, Agent, or Firm* — Biotech Beach Law Group, PC; Raymond Wagenknecht

(57) ABSTRACT

An implant having a base body, comprised either entirely or in part of a biocorrodible metallic material wherein at least the parts of the base body having the biocorrodible metallic material are at least partially covered with a coating of a crosslinked $CF_x$ layer that is nonpolymerized and has an F/C ratio in the range of 0.5 to 1.5.

7 Claims, No Drawings

US 8,801,778 B2

IMPLANT WITH A BASE BODY OF A BIOCORRODIBLE ALLOY

CROSS REFERENCE TO RELATED APPLICATIONS

This patent application is a continuation-in-part of U.S. patent application Ser. No. 12/339,965 filed Dec. 9, 2008, which claims priority to German Patent Application No. 10 2007 061 647.5, filed Dec. 20, 2007, the disclosure of which is incorporated herein by reference in its entirety.

FIELD OF THE INVENTION

The present disclosure relates to an implant with a base body consisting entirely or in part of a biocorrodible alloy. The present disclosure also provides a method for manufacturing such a stent.

BACKGROUND

Implants are used in a variety of embodiments in modern medical technology. Implants serve, among other things, to support blood vessels, hollow organs and duct systems (endovascular implants), to attach and temporarily secure tissue implants and tissue transplants, and for orthopedic purposes, for example, as nails, plates or screws.

Thus, for example, implantation of stents has become established as one of the most effective therapeutic measures in the treatment of vascular diseases. The purpose of stents is to provide a supporting function in the hollow organs of a patient. Stents of a traditional design, therefore, have a filigree supporting structure of metallic struts, which are present initially in a compressed form for introduction into the body and then are widened at the site of application. One of the main areas of application of such stents is for permanently or temporarily widening vascular constrictions, in particular, constrictions (stenoses) of the myocardial vessels, and then keeping the constricted areas open. In addition, aneurysm stents are also known in the art that, for example, serve to support damaged vascular walls.

The basic body of each implant, in particular, of stents, comprises an implant material. For purposes of the present disclosure, an implant material is a non-living material that is used for application in medicine and which interacts with biological systems. The basic prerequisites for use of a material as an implant material, which is in contact with the body's environment when used as intended, is that the material must be compatible with the body (biocompatibility). For purposes of the present disclosure, biocompatibility is the ability of a material to induce an appropriate tissue reaction in a specific application. This includes an adaptation of the chemical, physical, biological and morphological surface properties of an implant to the recipient tissue to obtain a clinically desired interaction. The biocompatibility of the implant material also depends on the chronological course of the reaction of the biosystem in which the implant is located. Irritation and inflammation, which may lead to tissue changes, may thus occur relatively rapidly. Biological systems react in different ways depending on the properties of the implant material. Depending on the reaction of the biosystem, the implant materials may be subdivided into bioactive, bioinert and degradable/absorbable materials. For purposes of the present disclosure, only degradable/absorbable metallic implant materials are of interest. For purposes of the present disclosure, these degradable/absorbable metallic implant materials are referred to hereinbelow as biocorrodible metallic materials.

The use of biocorrodible metallic materials is recommended, in particular, because, in most cases, the implant need only remain temporarily in the body to fulfill the medical purpose. Implants of permanent materials, i.e., materials that are not degraded in the body, are optionally removed again because there may be rejection reactions on the part of the body in the medium range and in the long term, even when there is a high biocompatibility.

One approach to avoid an additional surgical procedure thus consists of forming the implant entirely or in part of a biocorrodible metallic material. For purposes of the present disclosure, biocorrosion refers to microbial processes or simply processes caused by the presence of endogenous media leading to a gradual degradation of the structure comprising the material. At a certain point in time, the implant or at least the part of the implant made of the biocorrodible material loses its mechanical integrity. The degradation products are largely absorbed by the body. As in the case of magnesium, for example, in the best case the degradation products even have a positive therapeutic effect on the surrounding tissue. Small quantities of unabsorbable alloy constituents are tolerable as long as they are nontoxic.

Known biocorrodible metallic materials include, but are not limited to, pure iron and biocorrodible alloys of the group consisting of the main elements of magnesium, iron, zinc, molybdenum and tungsten. It is proposed in German Patent Application No. 197 31 021 that, among other things, medical implants should be made of a metallic material whose main component is an element from the group consisting of alkali metals, alkaline earth metals, iron, zinc and aluminum. Alloys based on magnesium, iron and zinc are described as being especially suitable. Secondary constituents of the alloys may be manganese, cobalt, nickel, chromium, copper, cadmium, lead, tin, thorium, zirconium, silver, gold, palladium, platinum, silicon, calcium, lithium, aluminum, zinc and iron. In addition, German Patent Application No. 102 53 634 describes the use of a biocorrodible magnesium alloy containing >90% magnesium, 3.7-5.5% yttrium, 1.5-4.4% rare earth metals and <1% remainder, which are suitable, in particular, for the production of an endoprothesis, e.g., in the form of a stent. Regardless of the advances that have been achieved in the field of biocorrodible metal alloys, the alloys known so far have only limited usability because of their corrosion behavior. The relatively rapid biocorrosion of the magnesium alloys, in particular, limits their field of use.

Traditional technical fields of use of molded bodies made of metallic materials, in particular, magnesium alloys, outside of medical technology usually require extensive suppression of corrosive processes. Accordingly, the purpose of most technical methods for improving corrosion performance is to completely inhibit corrosive processes. However, the goal of improving the corrosion performance of the biocorrodible metallic materials in the present disclosure lies not in complete suppression of corrosive processes but only in inhibition of corrosive processes. For this reason alone, most of the known measures for improving corrosion protection are not suitable. Furthermore, for a use in medical technology, toxicological aspects must also be taken into account. In addition, corrosive processes depend greatly on the medium in which the processes take place and, therefore, the findings about corrosion protection obtained under traditional environmental conditions in a technical (in vitro) environment should not be transferable to the processes in a physiological environment to an unlimited extent.

According to one approach of known technical methods for improving corrosion behavior (in the sense of increasing corrosion protection), a corrosion-preventing layer is produced on the molded body made of the metallic material. Known methods for creating a corrosion-preventing layer have been developed and optimized from the standpoint of technical use of the coated molded body, but not medical technical use in biocorrodible implants in a physiological environment. These known methods include, for example, applying polymers or inorganic cover layers, creating an enamel, chemical conversion of the surface, hot gas oxidation, anodizing, plasma sputtering, laser beam remelting, PVD methods, ion implantation or lacquering.

European Patent Application No. 0 993 308 describes a permanent stent coated by a PVD method with a carrier polymer to which perfluoroalkyl chains are bound. European Patent Application No. 0 560 849 describes an implant having a fluorinated polymer surface which is created by immersing the implant in a solution and then drying the implant. U.S. Pat. No. 5,246,451 discloses a plasma coating method for permanent vascular prostheses in which a polymer layer containing fluorine can be created by a plasma treatment. This polymer layer is then functionalized, again with the use of a plasma.

One feature of the present disclosure provides an improved or at least an alternative coating for an implant of a biocorrodible metallic material which produces a temporary inhibition but not complete suppression of corrosion of the material in a physiological environment.

SUMMARY

The present disclosure describes several exemplary embodiments of the present invention.

One aspect of the present disclosure provides an implant, comprising: a base body comprising a biocorrodible metallic material wherein at least the parts of the base body comprising the biocorrodible metallic material are at least partially covered with a coating of a crosslinked $CF_x$ layer that is nonpolymerized and has an F/C ratio in the range of 0.5 to 1.5.

Another aspect of the present disclosure provides a method for producing an implant having a base body comprised either entirely or in part of a biocorrodible metallic material, wherein at least the parts of the base body comprising the biocorrodible metallic material are at least partially covered with a coating of a crosslinked $CF_x$ layer that is nonpolymerized and has an F/C ratio in the range of 0.5 to 1.5, the method comprising (i) providing a plasma coating system; (ii) providing an implant blank having a base body comprising the biocorrodible metallic material either entirely or in part; and (iii) coating the surface of the blank in the plasma coating system by plasma treatment in the presence of one or more compounds selected from the group consisting of fluoroalkanes of the formula $C_nF_{2n+2}$, fluoroalkenes of the formula $C_nF_{2n}$, fluoroalkynes of the formula $C_nF_{2n-2}$ and cyclic fluorocarbon compounds with 3 to 10 carbon atoms where n=2 to 10, and maintaining the following conditions during the plasma treatment: a pressure in the range of 0.01 to 10 mbar, a flow rate in the range of 1 to 100 sccm, and either a power input in the range of 300 W to 1000 W in the case of a microwave plasma or a power input in the range of 10 W to 500 W in the case of a radiofrequency plasma.

One aspect of the present disclosure provides an implant having a base body consisting entirely or in part of a biocorrodible metallic material wherein at least the parts of the base body consisting of the biocorrodible metallic material are covered completely or partially with a coating of a crosslinked CFx layer that is nonpolymerized and has an F/C ratio in the range of 0.5 to 1.5.

In addition to the surface composition, the F/C ratio also provides information about the crosslinking components and/or the degree of crosslinking of the applied layer. A low F/C ratio is caused by a highly crosslinked F/C-containing layer. A high F/C ratio, such as that of commercial PTFE (F/C=2), indicates a chain-type layer with very little crosslinked F/C. The parts of the base body comprising the biocorrodible metallic material are preferably completely covered with the $CF_x$ layer. The F/C ratio makes it possible to control the corrosion behavior. At the same layer thickness, an increase in the F/C ratio leads to a reduction in corrosion rate.

It has been found that applying a coating of the aforementioned composition leads to the development of a protective layer that permanently inhibits corrosion, either largely or completely, in a physiological environment. In other words, in a physiological environment, corrosion of the implant nevertheless takes place, but at a definitely delayed rate.

According to one exemplary embodiment, the $CF_x$ layer has a layer thickness in the range of 1 nm to 10 µm. If the implant is a stent, then the layer thickness of the $CF_x$ layer is preferably in the range of 1 nm to 2 µm, in particular, 50 nm to 100 nm. With layer thicknesses below the stated lower limit, homogeneous coverage of the areas of the base body to be coated is no longer ensured making it difficult to establish the desired corrosion behavior in a reproducible manner. When the layer thickness is above the aforementioned limit, inherent stresses may occur within the layer, leading to inhomogeneities, which in turn can necessitate a reproducible establishment of the desired corrosion behavior. It is self-evident that the corrosion-inhibiting effect of the $CF_x$ layer increases with an increase in layer thickness. To achieve a predefinable corrosion behavior, those skilled in the art may proceed as described below.

DETAILED DESCRIPTION

Sample bodies are produced from the biocorrodible metallic material and are then coated by the method described in the present disclosure until achieving a predefinable layer thickness of the $CF_x$ layer. In this way, for example, five test bodies with different defined layer thicknesses can be produced, and their corrosion behavior can then be quantified (e.g., by determining the corrosion rate), allowing a qualitative prediction of the relationship between layer thickness and corrosion behavior. The resulting data for the corrosion behavior are compared with the desired corrosion behavior. If the comparison reveals significant deviations from each of the values obtained from the sample bodies, then the layer thickness is varied in additional sample bodies, starting from the nearest value. Ultimately those skilled in the art can determine a layer thickness for the desired corrosion behavior by routine processing of this optimization procedure.

The biocorrodible metallic material is preferably a biocorrodible alloy selected from the group consisting of elements including magnesium, iron, zinc, molybdenum and tungsten. In particular, the material is a biocorrodible magnesium alloy. For purposes of the present disclosure, an alloy is a metallic structure whose main component is magnesium, iron, zinc, molybdenum or tungsten. For purposes of the present disclosure, the main component is the alloy component whose amount by weight in the alloy is highest. The main component preferably amounts to more than 50 wt %, in particular, more than 70 wt %.

An especially preferred alloy is a magnesium alloy with the composition 5.2-9.9 wt % rare earth metals, including 3.7-5.5 wt % yttrium, and <1 wt % remainder, with magnesium accounting for the rest of the alloy to a total of 100 wt %. This magnesium alloy has already confirmed its special suitability in clinical trials; i.e., the magnesium alloy has shown a high biocompatibility, favorable processing properties and good mechanical characteristics. Through in vivo studies, it has been shown that the magnesium alloy is degraded and/or replaced by endogenous components. For purposes of the present disclosure, the collective term "rare earth metals" includes scandium (21), yttrium (39), lanthanum (57) and the 14 elements that follow lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71). In addition, magnesium alloys containing up to 6 wt % zinc are preferred. Furthermore, a magnesium alloy of the composition 0.5-10 wt % yttrium, 0.5-6 wt % zinc, 0.05-1 wt % calcium, 0-0.5 wt % manganese, 0-1 wt % silver, 0-1 wt % cerium and 0-1 wt % zirconium or 0-0.4 wt % silicon is especially preferred, where the amounts are based on wt % of the alloy, with magnesium and impurities due to the production process accounting for the remainder of the alloy up to 100 wt %.

The composition of the alloys of the elements magnesium, iron, zinc, molybdenum or tungsten is to be selected so that the alloys are biocorrodible. For purposes of the present disclosure, biocorrodible refers to alloys in which degradation/rearrangement takes place in a physiological environment so that the part of the implant consisting of this material is not present at all or at least not predominately. Artificial plasma as specified for biocorrosion tests according to EN ISO 10993-15:2000 (composition NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L) is used as the test medium for testing the corrosion behavior of an alloy in question. A sample of the alloy to be tested is stored in a sealed sample container with a defined amount of the test medium at 37° C. At intervals of a few hours to several months, based on the corrosion behavior to be expected, the samples are removed and examined for traces of corrosion in a way known in the art. The artificial plasma according to EN ISO 10993-15:2000 corresponds to a medium resembling blood and thus reproducibly achieves a physiological environment.

For purposes of the present disclosure, the term "corrosion" refers primarily to the reaction of a metallic material with its environment whereby a measurable change in the material is induced leading to an impairment of the function of the component if the material is used in a component. For purposes of the present disclosure, a corrosion system consists primarily of the corroding metallic material and a liquid corrosion medium, the composition of which mimics the conditions in a physiological environment, or is a physiological medium, in particular, blood. In terms of the material, factors such as the composition and pretreatment of the alloy, microscopic and submicroscopic inhomogeneities, boundary zone effects, temperature and mechanical stress state and, in particular, the composition of a layer covering the surface influence the corrosion. From the standpoint of the medium, the corrosion process is influenced by conductivity, temperature, temperature gradient, acidity, volume/surface ratio, concentration difference and flow rate.

Redox reactions take place at the phase boundary between the material and the medium. For a protective and/or inhibiting effect, the existing protective structures and/or the products of the redox reactions must develop a sufficiently dense structure against the corrosion medium, must have an increased thermodynamic stability based on the environment and must have little or no solubility in the corrosion medium. Adsorption and desorption processes take place in the phase boundary, or more precisely in a double layer developing in this region. The processes taking place in the double layer are characterized by the cathodic, anodic and chemical subprocesses taking place there. Deposits of foreign substances, impurities and corrosion products influence the corrosion process. The processes involved in corrosion are thus highly complex and either cannot be predicted at all or can only be predicted to a limited extent, especially in conjunction with a physiological corrosion medium, i.e., blood or artificial plasma, because comparative data are unavailable. For this reason alone, discovering a corrosion-inhibiting coating, i.e., a coating which serves to only temporarily reduce the corrosion rate of a metallic material of the composition defined above in a physiological medium is a measure that would be outside of the routine of those skilled in the art.

The corrosion process can be quantified by stating a corrosion rate. Prompt degradation is associated with a high corrosion rate and vice versa. Based on the degradation of the entire foreign body, a modified surface in the sense of the present disclosure will lead to a reduction in corrosion rate. In the case of coronary stents, preferably the mechanical integrity of the structure is maintained for a period of three months or more after implantation.

For purposes of the present disclosure, implants are devices introduced into the body by a surgical method or a minimally invasive procedure and comprise fastening elements for bones, e.g., screws, plates or nails, surgical suture material, intestinal clamps, vascular clips, prostheses in the area of hard and soft tissue, e.g., stents and anchoring elements for electrodes, in particular, pacemakers or defibrillators. The implant consists entirely or in part of the biocorrodible material. If the implant consists of the biocorrodible material only in part, this part must be coated accordingly.

The implant is preferably a stent. Stents of the traditional design have a filigree structure of metallic struts, which are first in a non-expanded state for introduction into the body and then are widened into an expanded state at the site of application. With stents, there are special requirements of the corrosion-inhibiting layer. The mechanical stress on the material during expansion of the implant has an influence on the course of the corrosion process, and it may be assumed that stress corrosion is increased in the stressed areas. A corrosion-inhibiting layer should take this into account. In addition, a hard corrosion-inhibiting layer might rupture during expansion of the stent and the development of cracks in the layer might be unavoidable on expansion of the implant. Finally, the dimensions of the filigree metallic structure are to be taken into account and, if possible, only a thin but uniform corrosion-inhibiting layer should be produced. It has now been found that application of the coating according to the present disclosure meets these requirements entirely or at least to a great extent.

Another aspect of the present disclosure provides a method for producing an implant with a base body which consists entirely or in part of a biocorrodible metallic material whereby at least the parts of the base body consisting of the biocorrodible metallic material are completely or partially covered with a coating of a crosslinked $CF_x$ layer that is nonpolymerized and has an F/C ratio in the range of 0.5 to 1.5. The method according to the present disclosure comprises the following steps:

(i) providing a plasma coating system and an implant blank having a base body which consists entirely or in part of the biocorrodible metallic material; and (ii) coating the surface of the blank in the plasma coating system by plasma treatment in the presence of one or more compounds selected from the group consisting of fluoroalkanes of the formula $C_nF_{2n+2}$, fluoroalkenes of the formula $C_nF_{2n}$, fluoroalkynes of the formula $C_nF_{2n-2}$, and cyclic fluorocarbon compounds with 3 to 10 carbon atoms where n=2 to 10, and under the following conditions during the plasma treatment:
a pressure in the range of 0.01 to 10 mbar,
a flow rate in the range of 1 to 100 sccm, and
a power input in the range of 300 W to 1000 W in the case of a microwave plasma or a power input in the range of 10 W to 500 W in the case of a radiofrequency plasma.

The method of the present disclosure is based on the finding that the coating of biocorrodible metallic materials for implants can be applied especially effectively with the help of a plasma method. In addition, the choice of the reactive gas for the plasma coating and of the operating parameters during the plasma treatment is an essential element of the method to arrive at the desired $CF_x$ layer.

For the plasma treatment, a traditional plasma coating system may be used. The implant to be coated should be situated outside of the active zone in the so-called "afterglow" of the plasma. Working in the afterglow has the advantage that no electric fields that could interfere with the process due to an unacceptable risk of overheating can be applied to the samples to be coated (e.g., a metallic stent).

The input power in the case of excitation of the plasma by microwaves is in the range of 500 W to 900 W.

According to one exemplary embodiment of the method, the prevailing pressure in the case of the radiofrequency plasma as well as the microwave plasma is in the range of 0.1 mbar to 5 mbar.

In addition, it is preferable if a chain length n of the fluoroalkanes, fluoroalkenes and fluoroalkynes or fluorocycloalkanes used is in the range of n=3 to n=6. For purposes of the present disclosure, cyclic fluorocarbon compounds with 3 to 10 carbon atoms comprise all ring compounds with a cyclic basic carbon structure of 3 to 10 carbons in which the free valences on the individual carbon atoms are occupied by fluorine. The cyclic fluorocarbon compounds may contain C—C double bonds and C—C triple bonds and may optionally form an aromatic system. Hexafluorobenzene is especially preferred.

Finally, it is preferable if the flow rate, which can be implemented via the carrier gas, is in the range of 30 to 60 sccm, in particular, 50 sccm.

Another aspect of the present disclosure provides an implant produced by the method described hereinabove.

The present disclosure is explained in greater detail below on the basis of an exemplary embodiment.

EXAMPLE

A stent of the commercially available magnesium alloy WE43 (according to ASTM) with a rare earth metal content of approximately 3 wt %, not including yttrium, and an yttrium content of approximately 4 wt % is introduced into a plasma coating system from the company, Plasma-finish GmbH. The stent is positioned in the coating system such that the stent is in the "afterglow" of the plasma to be generated. Then hexafluorobenzene $C_6F_6$ is supplied as the reactive gas at a flow rate of 50 sccm, with argon functioning as the carrier gas. The process pressure is 0.5 mbar. The plasma power input is regulated at 800 W with the plasma being excited by microwaves. The coating time is 2 minutes.

After removal of the stent, the resulting nonpolymerized but crosslinked $CF_x$ layer can be detected structurally with surface-sensitive methods. The F/C ratio is 0.6. The layer thickness is approximately 150 nm.

All patents, patent applications and publications referred to herein are incorporated by reference in their entirety.

What is claimed is:

1. An implant, comprising: a base body comprising a biocorrodible metallic material wherein at least the parts of the base body comprising the biocorrodible metallic material are at least partially covered with a coating of a crosslinked carbon fluoride material having the general formula $CF_x$ and selected from the group consisting of fluoroalkanes of the formula $C_nF_{2n+2}$, fluoroalkenes of the formula $C_nF_{2n}$, fluoroalkynes of the formula $C_nF_{2n-2}$ and cyclic fluorocarbons, where the carbon fluoride material has between 3 and 10 carbon atoms and where n=2-10, wherein x is the ratio of F atoms to C atoms and is between 0.5 and 1.5, wherein the crosslinked carbon fluoride material is nonpolymerized, and wherein the amount of coating allows for controlled corrosion of the biocorrodible metallic material.

2. The implant of claim 1, wherein the biocorrodible metallic material is a biocorrodible alloy containing a metal selected from the group consisting of magnesium, iron, zinc, molybdenum and tungsten.

3. The implant of claim 2, wherein the biocorrodible material is a magnesium alloy.

4. The implant of claim 1, wherein the implant is a stent.

5. The implant of claim 1, wherein the $CF_x$ layer has a layer thickness in the range of 1 nm to 10 μm wherein the layer has a uniform thickness.

6. The implant of claim 5, wherein the implant is a stent and the $CF_x$ layer has a layer thickness in the range of 1 nm to 2 μm.

7. The implant of claim 6, wherein the $CF_x$ layer has a layer thickness in the range of 50 nm to 100 nm.

* * * * *